(12) United States Patent
Wolf, II

(10) Patent No.: US 12,708,770 B2
(45) Date of Patent: Aug. 18, 2026

(54) FEED FORWARD CONTROL SYSTEM FOR A SPINAL CORD STIMULATION SYSTEM AND METHOD OF USE

(71) Applicant: Wavegate Corporation, Lake Charles, LA (US)

(72) Inventor: Erich W. Wolf, II, Lake Charles, LA (US)

(73) Assignee: Wavegate Corporation, Lake Charles, LA (US)

( * ) Notice: Subject to any disclaimer, the term of this patent is extended or adjusted under 35 U.S.C. 154(b) by 335 days.

(21) Appl. No.: 18/355,126

(22) Filed: Jul. 19, 2023

(65) Prior Publication Data

US 2024/0024680 A1 Jan. 25, 2024

Related U.S. Application Data

(60) Provisional application No. 63/368,791, filed on Jul. 19, 2022.

(51) Int. Cl.

| | |
|---|---|
| ***A61N 1/36*** | (2006.01) |
| ***A61B 5/00*** | (2006.01) |
| ***A61B 5/11*** | (2006.01) |
| ***A61N 1/05*** | (2006.01) |
| *A61N 1/02* | (2006.01) |

(52) U.S. Cl.

CPC ........ *A61N 1/36062* (2017.08); *A61B 5/1116* (2013.01); *A61B 5/686* (2013.01);

(Continued)

(58) Field of Classification Search

CPC ............ A61N 1/36062; A61N 1/36071; A61N 1/36139; A61N 1/36142; A61N 1/0551;

(Continued)

(56) References Cited

U.S. PATENT DOCUMENTS

| | | | |
|---|---|---|---|
| 9,550,063 | B2 | 1/2017 | Wolf, II |
| 2003/0120323 | A1 | 6/2003 | Meadows et al. |

(Continued)

FOREIGN PATENT DOCUMENTS

| | | |
|---|---|---|
| WO | 2020251899 | 12/2020 |
| WO | 2021062345 | 4/2021 |

OTHER PUBLICATIONS

Neuman, M. R. “Biopotential Electrodes.” The Biomedical Engineering Handbook: Second Ed. Joseph D. Bronzino; Boca Raton: CRC Press LLC, 2000 (Year: 2000).*

(Continued)

*Primary Examiner* — Pamela M. Bays

(74) *Attorney, Agent, or Firm* — Schultz & Associates, P.C.

(57) ABSTRACT

The system incorporates a feed forward control system which automatically adjusts mean stimulation current to maintain consistent dosing of electrical current applied to the spinal cord despite motion of the spinal cord relative to the epidural electrode array. Optical boundary conditions are captured using a sample and hold circuit when the spinal cord is in its most dorsal position (supine patient position) and most ventral position (prone or sitting positions). Optimal mean stimulation current is manually set for these two ordinal positions during setup. During operation, the mean current is actively modulated by interpolating the mean current between the two current boundary conditions using a nominally inverse linear relation to the instantaneous optical reflectance which is bounded by the optical boundary conditions.

14 Claims, 10 Drawing Sheets

(52) U.S. Cl.
CPC ....... *A61N 1/0551* (2013.01); *A61N 1/36139* (2013.01); *A61N 1/36157* (2013.01); *A61B 5/4561* (2013.01); *A61B 5/4566* (2013.01); *A61B 5/6867* (2013.01); *A61N 1/025* (2013.01); *A61N 1/36071* (2013.01)

(58) Field of Classification Search
CPC .. A61N 1/36157; A61N 1/025; A61B 5/1116; A61B 5/4538; A61B 5/686; A61B 5/6867
See application file for complete search history.

(56) References Cited

U.S. PATENT DOCUMENTS

| | | | | |
|---|---|---|---|---|
| 2012/0095525 | A1 | 4/2012 | Wolf, II | |
| 2018/0256906 | A1* | 9/2018 | Pivonka ................. | A61N 1/378 |
| 2019/0269917 | A1 | 9/2019 | Courtine et al. | |
| 2021/0370070 | A1 | 12/2021 | Debarros et al. | |
| 2022/0096848 | A1 | 3/2022 | Hareland et al. | |
| 2023/0372685 | A1* | 11/2023 | Manbachi .............. | A61B 5/076 |

OTHER PUBLICATIONS

Written Opinion of the International Searching Authority for PCT/US23/70514, Form PCT/ISA/237. (6 Pages). Mail date Dec. 13, 2023 (Year: 2023).*

Wolf, II "Dynamic Detection of Spinal Cord Position During Postural Changes Using Near-Infrared Reflectometry", ScienceDirect, Apr. 2015.

* cited by examiner

FEED FORWARD CONTROL SYSTEM FOR A SPINAL CORD STIMULATION SYSTEM AND METHOD OF USE

CROSS-REFERENCE TO RELATED APPLICATIONS

This application claims priority benefit to U.S. Provisional Patent Application No. 63/368,791, filed Jul. 19, 2022. The patent application identified above is incorporated here by reference in its entirety to provide continuity of disclosure.

FIELD OF THE INVENTION

The present invention relates generally to spinal cord stimulation systems.

BACKGROUND OF THE INVENTION

Neuromodulation has been defined by the International Neuromodulation Society as "the alteration of nerve activity through targeted delivery of a stimulus, such as electrical stimulation or chemical agents, to specific neurological sites in the body". Although in the broadest sense neuromodulation refers to anything that modulates nerve activity (e.g. neurotransmitters, magnetic fields, etc.), in the clinical setting this term most commonly implies a spinal cord stimulation (SCS) treatment using an implanted electrical device.

SCS alters nerve functioning by stimulating the spinal cord. Electrodes are surgically implanted in the spine near the spinal cord and are used to broadcast a stimulation signal. The signal induces complex electrochemical reactions in the nervous system that can produce an analgesic effect.

SCS is typically delivered through an implanted pulse generator (IPG). Most IPG's are battery powered and must be recharged or replaced periodically. A handheld remote device serves to control the IPG through radio signals. The IPG provides a stimulation signal through one or more implanted leads which include one or more electrodes.

The electrodes are exposed contacts fixed to the distal ends of the leads. The contacts can be activated individually as either cathodes or anodes, by selective programming a defined pattern of electrodes can be activated to transmit any number of waveform signals.

The leads can be percutaneous leads or paddle arrays. One or more percutaneous lead arrays may be inserted through the skin using Touhy needle. They are typically cylindrical and have a diameter of only 1-2 mm.

Paddle arrays are larger than percutaneous leads and include a flexible plastic sheet in which the electrodes are embedded. Paddle arrays are installed through a laminectomy.

FIG. 1 shows a detail of electrode array 30 including electrode contacts 35 sealed into elastomeric housing 36. Each electrode contact has a separate electrical conductor in electrode leads 31 so that the current to each contact may be independently controlled. Independent control allows the stimulation signal to be varied top to bottom and left to right, along the array.

In FIG. 2, spinal column 1 is shown to have a number of vertebrae, categorized into four sections or types: lumbar vertebrae 2, thoracic vertebrae 3, cervical vertebrae 4 and sacral vertebrae 5. Cervical vertebrae 4 include the 1st cervical vertebra (C1) through the 7th cervical vertebra (C7). Just below the 7th cervical vertebra is the first of twelve thoracic vertebrae 3 including the 1st thoracic vertebra (T1) through the 12th thoracic vertebra (T12). Just below the 12th thoracic vertebrae, are five lumbar vertebrae 2 including the 1st lumbar vertebra (L1) through the 5th lumbar vertebra (L5), the 5th lumbar vertebra being attached to sacral vertebrae 5 (S1 to S5). Sacral vertebrae 5 being naturally fused together in the adult.

In FIGS. 3 and 4, representative vertebra 10, a thoracic vertebra, is shown to have a number of notable features which are in general shared with lumbar vertebrae 2 and cervical vertebrae 4. The thick oval segment of bone forming the anterior aspect of vertebra 10 is vertebral body 12. Vertebral body 12 is attached to bony vertebral arch 13 through which spinal nerves 11 run. Vertebral arch 13, forming the posterior of vertebra 10, is comprised of two pedicles 14, which are short stout processes that extend from the sides of vertebral body 12 and bilateral laminae 15. The broad flat plates that project from pedicles 14 join in a triangle to form a hollow archway, spinal canal 16. Spinous process 17 protrudes from the junction of bilateral laminae 15. Transverse processes 18 project from the junction of pedicles 14 and bilateral laminae 15. The structures of the vertebral arch protect spinal cord 20 and spinal nerves 11 that run through the spinal canal. Surrounding spinal cord 20 is dura 21 that contains cerebrospinal fluid (CSF) 22. Epidural space 24 is the space within the spinal canal lying outside the dura.

Referring to FIGS. 2, 3 and 4, IPG 39 typically includes pulse generator 32 operatively connected to digital controller 33. Pulse generator 32 delivers electrical stimuli to the spinal cord, typically within the thoracic region, through electrode lead 31 to electrode array 30. Electrode array 30 is typically positioned in epidural space 24 between dura 21 and the walls of spinal canal 16 towards the dorsal aspect of the spinal canal nearest bilateral laminae 15 and spinous process 17.

Controlling the amplitude of the stimulating electrical current is paramount to success of spinal cord stimulation. Applying inadequate current will fail to depolarize the targeted neurons, rendering the treatment ineffective. Conversely, application of too strong a current will depolarize the targeted neurons, but also stimulate additional cell populations which can render the perception of a noxious stimulation.

Establishing a consistent, therapeutic, and non-noxious level of stimulation is predicated upon establishing an ideal current density within the spinal cord's targeted neurons. Fundamentally, this should be a simple matter of establishing an optimal electrode current given the local bulk conductivity of the surrounding tissues. But, in practice, the optimal electrode current changes as a function of patient position and activity due to motion of the spinal cord as the spinal cord floats in cerebrospinal fluid within the spinal canal. Significant changes in distance between the epidural electrode array and the targeted spinal cord neurons have been shown to occur. Consequently, it is preferred to dynamically adjust the electrode stimulating current as a function of distance between the electrode array and the spinal cord.

Dynamic modulation of spinal cord stimulator electrode current as a function of distance between the electrode array and the spinal cord thus has several benefits. Too high a stimulation current can be avoided, thus reducing the prospects of noxious stimulation and potentially reducing device power consumption. Too low a stimulation current can be avoided, thus eliminating periods of inadequate stimulation and compromised therapeutic efficacy.

One such system that dynamically adjusts the stimulation signal is described in U.S. Pat. No. 9,550,063 to Wolf, II, which is incorporated herein by reference for all purposes. Wolf describes an IPG which delivers pulses of electrical current to an electrode array, which stimulates targeted neurons within the ascending tracts of the spinal cord. In general, the amplitude of the stimulation signal is controlled by an optical feedback signal which indicates how far the spinal cord is from the electrodes.

A challenge to SCS treatment is setting patient specific stimulation parameters, such as amplitude, frequency and pulse width. The dimensions of the vertebrae and the spinal column can vary by as much as 20% to 25% from patient to patient, rendering it necessary to adjust and optimize these parameters. These variations make calibration of the stimulation current levels difficult because they directly affect stimulation current density at the spinal cord. Anatomical variations such as blood vessels, epidural fat, and scar tissue can affect both the bulk resistivity and the optical environment within the epidural space. Thus, there is a need for a calibration process for IPGs which utilize optical control systems for automated adjustment of stimulation current.

SUMMARY OF THE INVENTION

This disclosure describes an IPG system that cooperates with an external system manager to deliver a stimulation signal. The IPG incorporates a novel control system that automatically adjusts the stimulation signal current and addresses optical calibration to improve analgesic efficacy and extend IPG battery life.

A control system for an IPG is disclosed. The control system requires both optical and stimulation boundary conditions. The optical reflectance upper and lower boundary conditions occur in the supine and prone positions, respectively. Other patient postures which produce extremes of optical reflectance may be substituted. In the context of this disclosure, the term "prone position" will refer to any patient posture where the spinal cord is in its most ventral position and is furthest away from the reflectometer. Likewise, the term "supine position" will refer to any patient posture where the spinal cord is in its most dorsal position and is nearest the reflectometer. Each boundary condition requires a single optical measurement at which patient feedback is solicited to determine the optimal stimulation current required to produce analgesia. The stimulation current is then clipped at each upper and lower boundary condition, thereby ensuring patient safety and promoting battery longevity. Alternatively, stimulation current may be clipped at just the upper boundary condition.

In use, a light signal, $V_P$, is injected into an optical fiber in an electro-optical lead toward the spinal canal. Once reaching the spinal canal, a portion of the light is reflected by the spinal cord and returned along the same fiber toward a reflectometer, such as a photo diode. The reflectometer generates a signal, R(t), indicating the strength of the reflected signal. The reflected signal is routed to a first sample and hold circuit to calibrate the optical reflectance for the prone position, $R_{prone}$ (a local minimum optical boundary condition) and a second sample and hold circuit to calibrate the optical reflectance for the supine position, $R_{supine}$ (a local maximum optical boundary condition).

In a summation block, $R_{prone}$ is subtracted from R(t) to remove the baseline reflectance offset to arrive at $R(t)_{corr}$. With the patient in the prone position, the mean stimulation current across the electrode array is manually programmed to patient preference to optimize analgesic effect. At this point, a third sample and hold circuit is set indicating the stimulation current, $S_{high}$ (a local maximum stimulation current boundary condition). The current may then be ramped up slowly while the patient is monitored for indication of a just notable difference (JND), at which the difference in current relative to $S_{high}$ is recorded as $I_{jnd}$.

With the patient placed in the supine position, a second sample and hold circuit is set to record the optical reflectance in the supine position, $R_{supine}$. In a second summation block, $R_{prone}$ is subtracted from $R_{supine}$ to determine $R_{range}$. $R(t)_{corr}$ is then divided by $R_{range}$ to derive a normalized signal nominally in the range between 0 and 1. Spinal cord acceleration or momentum can push the spinal cord beyond the physical positions used to define the optical boundary conditions of the supine or prone position. Thus, the reflectance output is clipped to the respective supine or prone value to arrive at R'. R' is then inverted (subtracted from 1) to provide a signal (1−R'). In the supine position, a stimulation current is manually ramped up slowly, while the patient is monitored, again, for the indication of a just notable difference.

With the patient in the supine position, the mean stimulation current across the electrode array is manually programmed to patient preference to optimize analgesic effect in this posture. A fourth sample and hold circuit is set indicating the stimulation current, $S_{low}$ (a local minimum stimulation current boundary condition).

$S_{low}$ is subtracted from $S_{high}$ resulting in $S_{range}$.

(1−R') is then multiplied by $S_{range}$ and added to $S_{low}$ resulting in signal S(t).

Signal S(t), responsive to the reflectometer signal R(t) is used to drive a current source which in turn, develops a current I(t), which is used to drive the electrodes.

BRIEF DESCRIPTION OF THE DRAWINGS

In the detailed description of the preferred embodiments presented below, reference is made to the accompanying drawings.

DETAILED DESCRIPTION OF THE INVENTION

In the description that follows, like parts are marked throughout the specification and figures with the same numerals, respectively. The figures are not necessarily drawn to scale and may be shown in exaggerated or generalized form in the interest of clarity and conciseness. Unless otherwise specified, all uses of the term "about" refer to ±20%.

Figure 1:
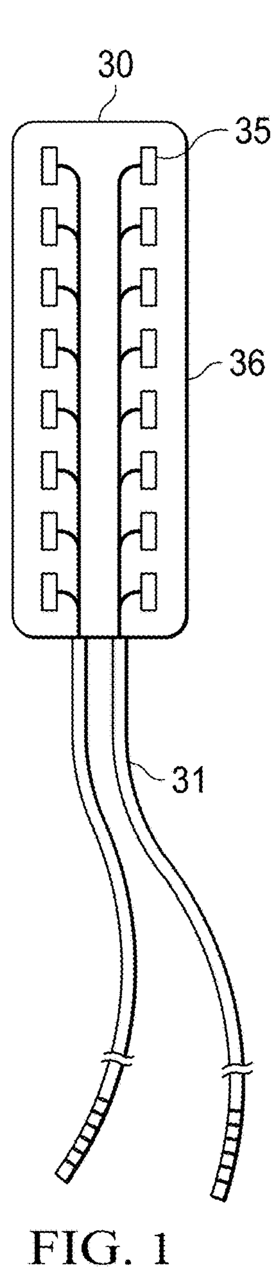
FIG. 1 shows a prior art paddle lead for spinal cord stimulation.
Figure 2:
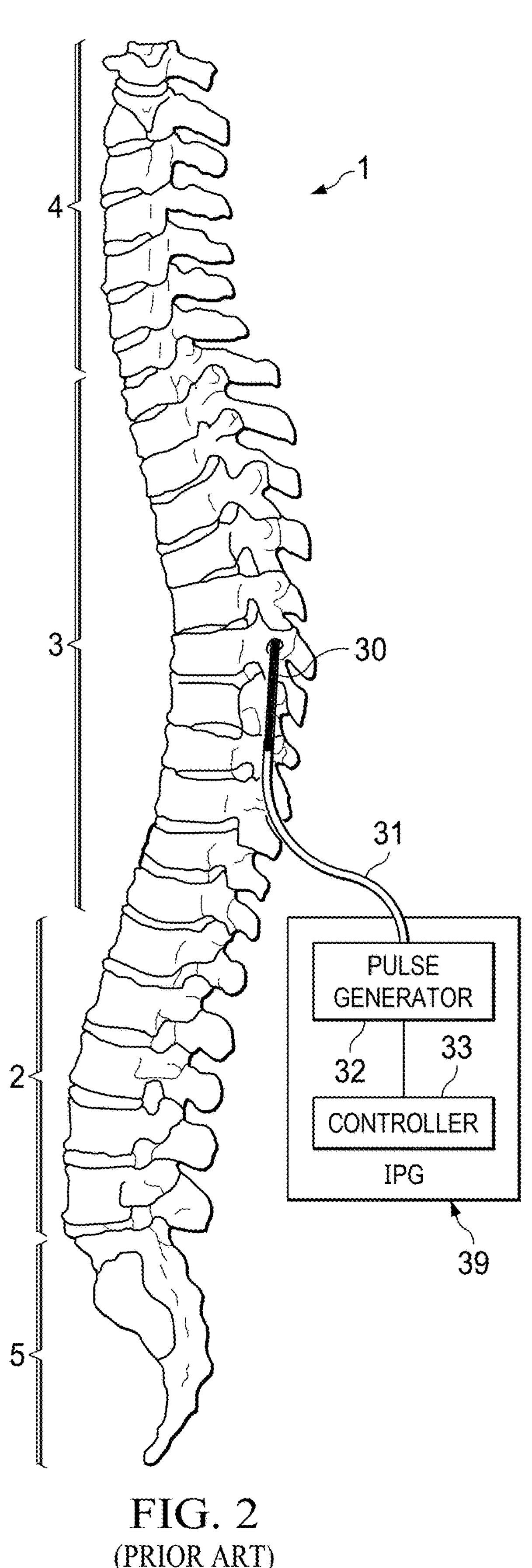
FIG. 2 is a side view of the human spine showing the approximate position of an electrode array for spinal cord stimulation of the prior art.
Figures 3, 4:
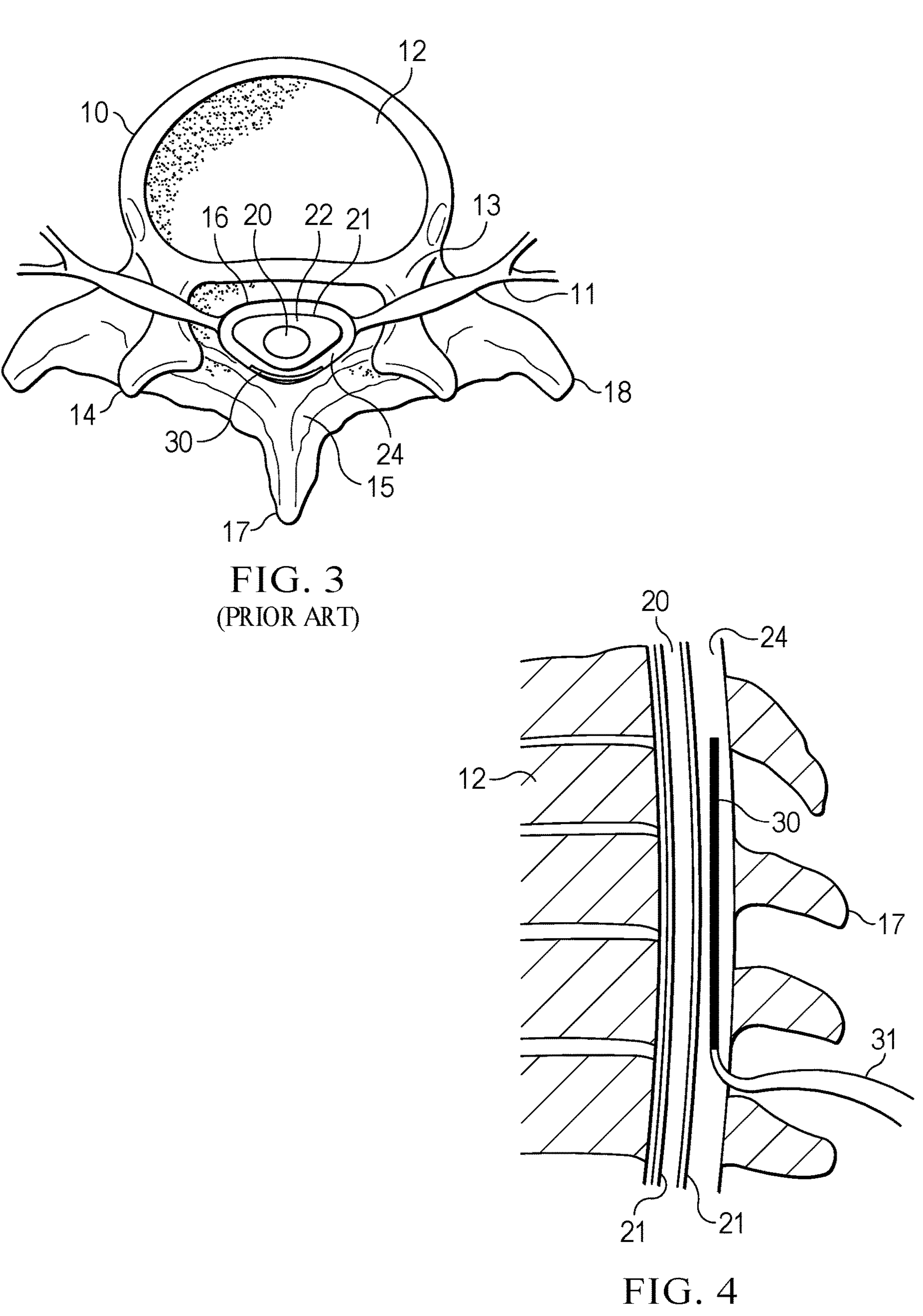
FIG. 3 shows an axial view of a thoracic vertebra indicating the position of the spinal cord and an electrode array for spinal cord stimulation of the prior art.
FIG. 4 shows a sagittal cross-sectional view of the human spine showing the approximate position of an electrode array for spinal cord stimulation of the prior art.
Figure 5:
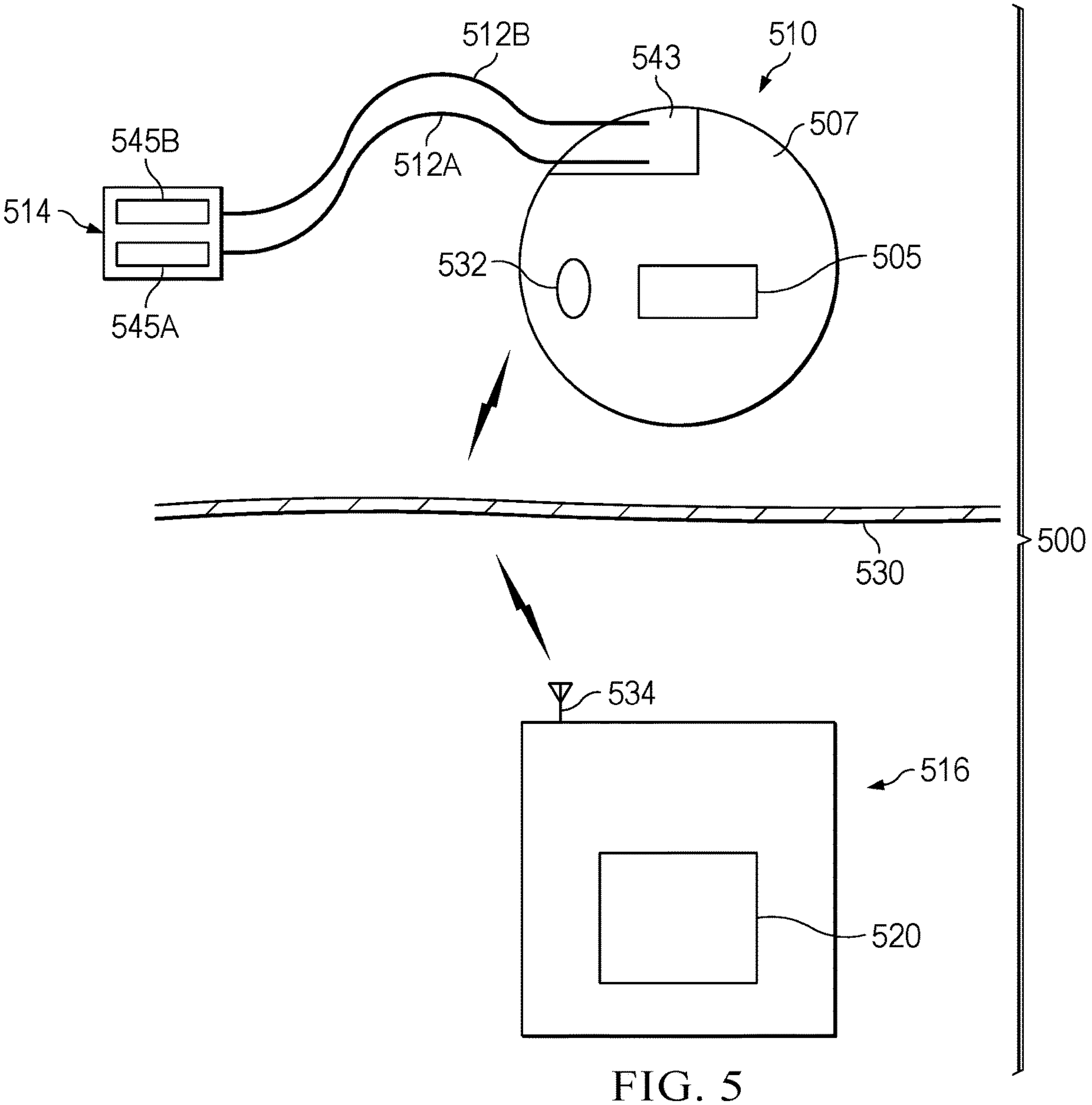
FIG. 5 shows a schematic of an IPG and external control system of a preferred embodiment.

Referring then to FIG. 5, preferred SCS system 500 comprises IPG 510 implanted subcutaneously beneath skin surface 530.

In summary, IPG 510 comprises controller 505, operatively connected to external system manager 516. The IPG and the external system manager communicate by transcutaneous radio signals, transmitted to and from RF antennas 532 and 534, as will be further described.

IPG 510 is preferably battery operated and contained in hermetically sealed case 507, which provides for long term subcutaneous implantation. IPG 510 includes controller 505 operatively connected to optical processing assembly 543. Optical processing assembly 543 is operatively connected to leads 512A and 512B. Leads 512A and 512B terminate in electrode arrays 545A and 545B in paddle array 514. In another embodiment, the electrode arrays may be on percutaneous leads, as previously described. Leads 512A and 512B further include optical transmission fibers, (not shown), which communicate light signals from optical processing assembly 543 to the electrode array where they illuminate the spinal cord and are reflected back to the optical processing assembly. The optical processing assembly converts reflected light signals into variable electrical current signals, which are used to determine the distance of the spinal cord from the electrode arrays. Controller 505 uses the light signals to modulate an electrical stimulation signal that is sent through the leads to the electrodes, as will be further described.

External system manager 516 includes controller 520, operatively connected to RF antenna 534.

In use, controller 520 includes a set of instructions which aid in collecting feedback from the patient as to the efficacy of various stimulation signal types. The feedback is processed to generate a set of operational parameters which are returned to the IPG wirelessly from RF antenna 532, as will be further described.

Figure 6A:
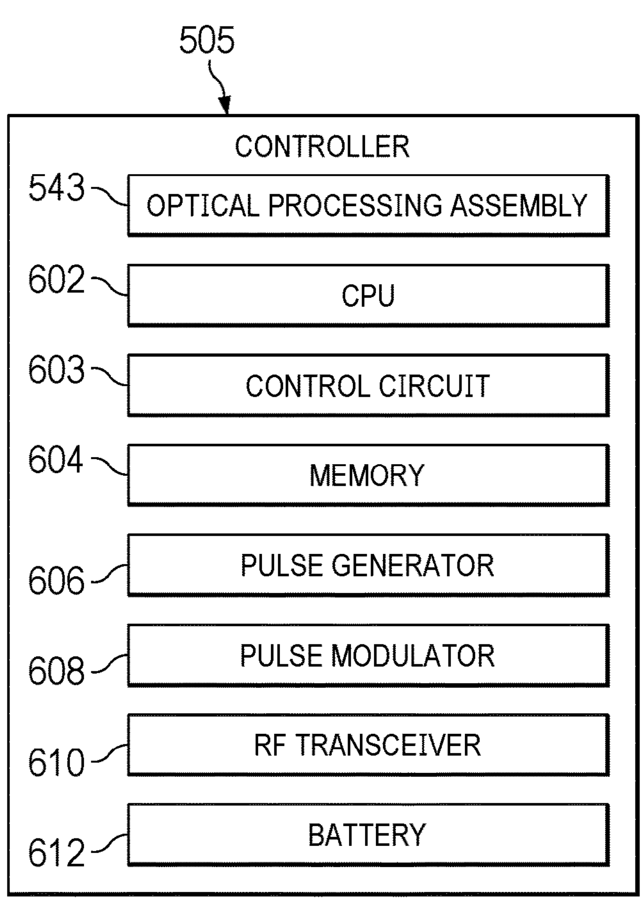
FIG. 6A is an architecture diagram of a preferred embodiment of an IPG.

Referring to FIG. 6A, controller 505 will be further described. Controller 505 comprises CPU 602 including onboard memory 604. The memory contains instructions which, when executed, provide the functions of the IPG. Controller 505 is operatively connected to control circuit 603, for monitoring of the reflectometer signal, as will be further described. Preferably, control circuit 603 is implemented using the threshold functions of multimodal front end part no. ADP4100, available from Analog Devices, Inc. of Wilmington, Massachusetts. Controller 505 is also operatively connected to optical processing assembly 543, for use in modulating the stimulation signal, and to RF transceiver 610, for transmission of status signals and reception of control parameters. CPU 602 is further connected to pulse modulator 608 and pulse generator 606 for generation and transmission of stimulation signals to the electrodes in certain alternate embodiments. All components are operatively connected to battery 612, which provides current to operate the IPG.

CPU 602 receives real time optical reflectance information with a feed forward control system to automatically set the stimulation current level for each electrode. The stimulation current level is calculated digitally and transmitted to pulse generator 606 and pulse modulator 608. Pulse modulator 608 then provides the requisite current to each of the electrodes. The stimulation current level may also be automatically calculated and generated by an analog version of the control circuit, as will be further described.

Figure 6B:
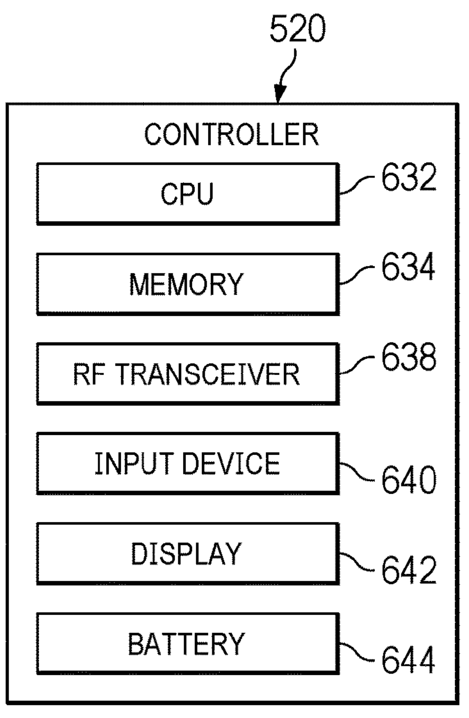
FIG. 6B is an architecture diagram of a preferred embodiment of the external control system.

Referring to FIG. 6B, controller 520 will be further described. Controller 520 includes CPU 632 connected to RF transceiver 638, display 642, input device 640, and memory 634. In the preferred embodiment, display 642 is a low power liquid crystal display adapted to show the current operational state of the system. Input device 640 is a simple push button contact array which is constantly monitored by CPU 632. Memory 634 is preferably onboard CPU 632 and stores instructions which, when executed, operate the external system manager. In the preferred embodiment, RF transceiver 638 is a low power transmitter/receiver combination. In the preferred embodiment, all components of the controller draw power from battery 644.

In another preferred embodiment, the components of controller 520 may be included in a personal computer, such as a laptop or cell phone, which transmits and receives RF signals containing data and instructions via MICS, WiFi, infrared or Bluetooth protocols.

Figure 7:
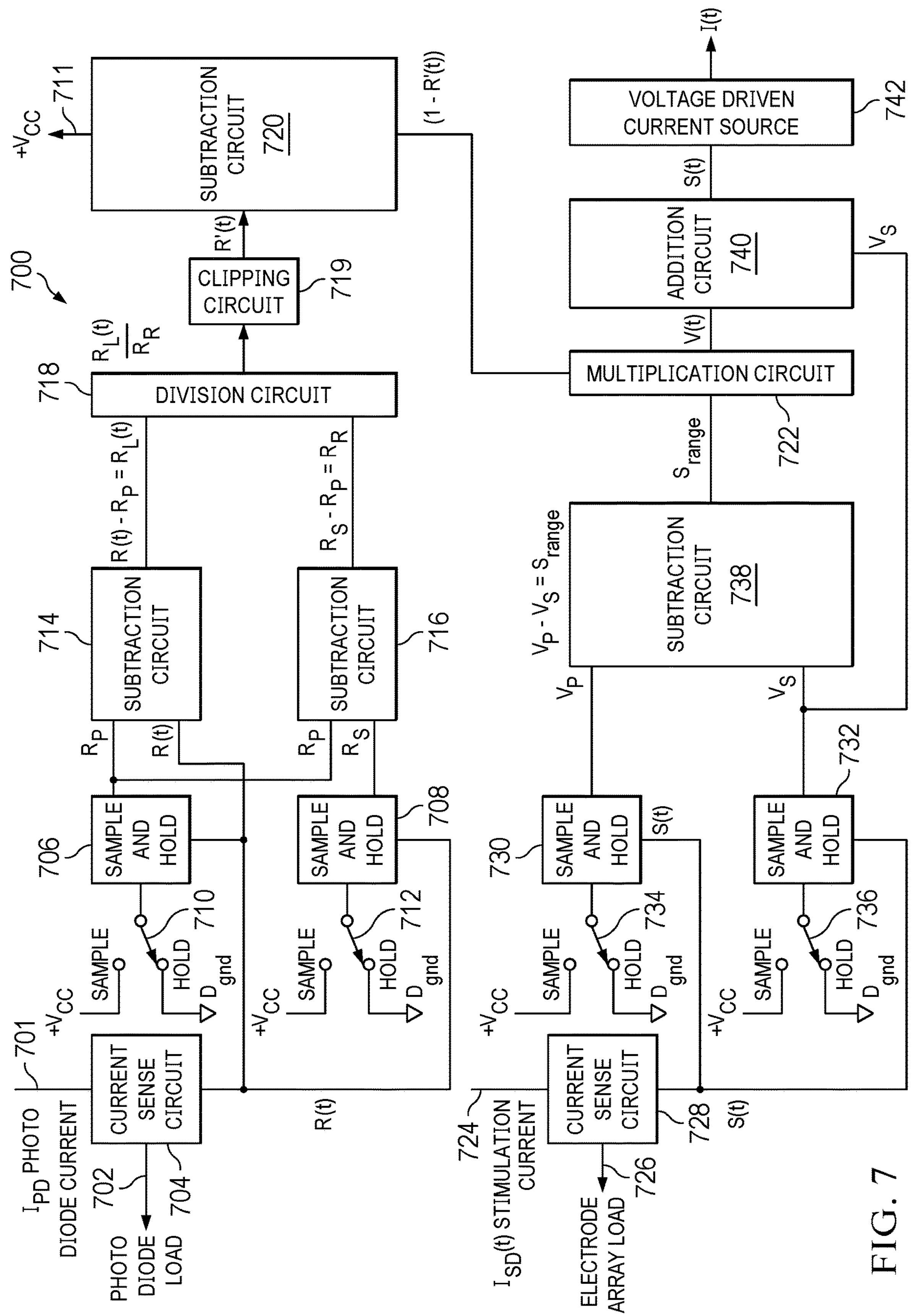
FIG. 7 is an architecture diagram showing signal flow through an analog circuit of a preferred embodiment.

Referring then to FIG. 7, block diagram 700 showing signal flow for a preferred analog embodiment of control circuit 603 will be further described.

Current sense circuit 704 is interposed between photo diode current source 701, $I_{PD}$, and photo diode load 702. Current sense circuit 704 produces voltage signal R(t) indicative of the amount of light incident on the photodiode. Current sense circuit 704 is operatively connected to sample and hold circuit 706, sample and hold circuit 708, and subtraction circuit 714, thereby distributing the R(t) signal to each of these circuits. The sample and hold circuit 706 command input is further connected to switch 710 whereby R(t) can be sampled momentarily during application of a digital logic "sample" command and is otherwise in a "hold" state. Likewise, the sample and hold circuit 708 command input is further connected to switch 712 whereby it can be similarly controlled.

Sample and hold circuit 706 output is operatively connected to subtraction circuit 714 and subtraction circuit 716. With the patient in the prone position, the sample and hold circuit input is briefly asserted to "sample" then returned to "hold" to capture the optical reflectance in the prone patient position $R_P$. Signal $R_P$ is indicative of the light incident on the photo diode when the patient is in the prone position, and which is distributed to subtraction circuit 714 and subtraction circuit 716. Likewise, with the patient in the supine position, sample and hold circuit 708 stores voltage signal, $R_S$, which is indicative of the light incident on the photo diode when the patient is in the supine position, and which is distributed to subtraction circuit 716. $R_P$ and $R_S$ are optical boundary conditions corresponding to minimum and maximum reflectance, respectively.

Subtraction circuit 714 produces a voltage signal, $R_L(t)$, which is the difference between $R_P$ and R(t) signals and varies with time. Likewise, subtraction circuit 716 produces a voltage signal, $R_R$, which is the difference between the $R_S$ and $R_P$ signals. This difference is indicative of the range over which reflected light signal varies between the prone and supine positions.

Division circuit 718 is operatively connected to subtraction circuit 714 and subtraction circuit 716. Division circuit 718 divides the $R_L(t)$ signal by the $R_R$ signal, thereby producing a signal which is normalized to unity.

The output of division circuit 718 is connected to clipping circuit 719. Clipping circuit 719 limits the output signal, R'(t), to a range between 0 and 1.

The output of clipping circuit 719 is operatively connected to subtraction circuit 720, thereby, distributing the R'(t) signal to that circuit. Subtraction circuit 720 is further operatively connected to voltage reference source, $V_{CC}$, 711. Subtraction circuit 720 produces a voltage output signal (1−R'(t)), which is the difference between 1 and R'(t), and distributes that signal to multiplication circuit 722, as will be further described. The subtraction circuit effectively inverts the R'(t) signal to account of the fact that the stimulation current must be generally inversely proportional to the reflected light signal.

Current sense circuit 728 is operatively connected to stimulation current source 724, $I_{SD}(t)$, driving the electrode array. Current sense circuit 728 is further connected to electrode array load 726. Current sense circuit 728 produces a voltage signal, S(t), indicative of the mean current through the electrodes, and distributes that signal to sample and hold circuit 730 and sample and hold circuit 732.

Sample and hold circuit 730 is operatively controlled by switch 734. Sample and hold circuit 730 produces a voltage signal, $V_P$, indicative of the optimized mean stimulation current required when the patient is in the prone position and distributes that signal to subtraction circuit 738.

Likewise, sample and hold circuit 732 is operatively controlled by switch 736. Sample and hold circuit 732 produces voltage signal, $V_S$, indicative of the optimal stimulation current required while the patient is in the supine position, and distributes that signal to subtraction circuit 738 and addition circuit 740, as will be further described.

Subtraction circuit 738 produces signal, $S_{range}$, which is the difference between the $V_P$ signal and the $V_S$ signal, and distributes the $S_{range}$ signal to multiplication circuit 722. $S_{range}$ is indicative of the range over which the stimulation current must vary between the prone and supine positions.

Multiplication circuit 722 produces signal, V(t), which is the product of the unity normalized (1−R'(t)) signal and the $S_{range}$ signal and distributes that signal to addition circuit 740. Multiplication circuit 722 effectively scales the range of the stimulation current to match the inverse of the reflected light signal.

Addition circuit 740 adds the $V_S$ signal to the $V_T$ signal to produce voltage signal, S(t), and distributes that signal to voltage driven current source 742.

Voltage driven current source 742 produces a mean current signal I(t), which is proportional to the voltage signal S(t). The I(t) current signal is used to drive the electrode array, as will be further described.

Figure 8:
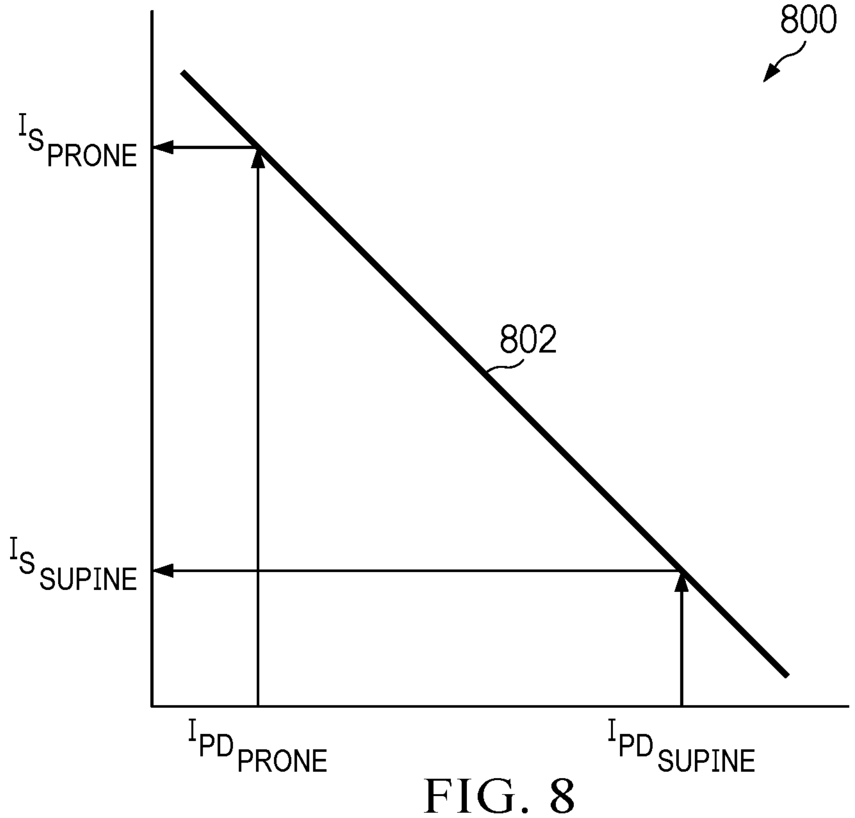
FIG. 8 is a graph of a preferred relationship between reflectometer current and stimulation current.

Referring then to FIG. 8, the feed forward relationship between the stimulation current "$I_S$" and the optical reflectance, indicated by the photo diode current, "$I_{PD}$" will be further described.

Graph 800 plots $I_{PD}$ on the x-axis and $I_S$ on the y-axis. The relationship between the photo diode current $I_{PD}$ and the stimulation current $I_S$ can be modeled as linear, with an inverse slope. Line 802 is defined by two points. The first point is defined by the photo diode current in the prone position, "$I_{PDprone}$", and the optimized stimulation current in the prone position "$I_{Sprone}$". The second point is defined by the photo diode current in the supine position, "$I_{PDsupine}$" and the stimulation current in the supine position "$I_{Ssupine}$".

The equation of line 802 takes the following form:

$$I_S = MI_{PD} + B$$

Where:

$$M = \frac{I_{SS} - I_{SP}}{I_{PDS} - I_{PDP}};\text{ and}$$

$$B = I_{SP} - \left(\frac{I_{SS} - I_{SP}}{I_{PDS} - I_{PDP}}\right) I_{PDP}.$$

Figure 9A:
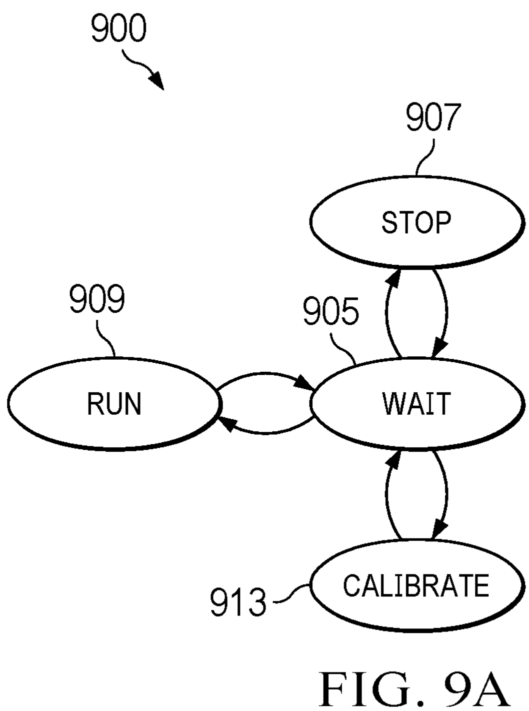
FIG. 9A is a state diagram of a preferred system.

Referring to FIG. 9A, state chart 900 will be further described. State chart 900 defines the various states in which the system may be found during operation. Preferably, external system manager 516 displays the various states in which the system is active and sends instructions to and receives feedback from IPG 510 confirming the state of the system.

Upon power up, both IPG 510 and external system manager 516 enter a wait state 905. During wait state 905, external system manager 516 displays a menu on display 642 indicating one of stop state 907, run state 909, or calibrate state 913. IPG 510 simply waits for commands. Upon receiving a stop selection, the external system manager enters stop state 907 and returns to wait state 905. Likewise, upon receiving a run selection, external system manager 516 enters run state 909 and then returns to wait state 905. Upon receipt of a calibrate selection, external system manager 516 enters calibrate state 913 and returns to wait state 905.

Figure 9B:
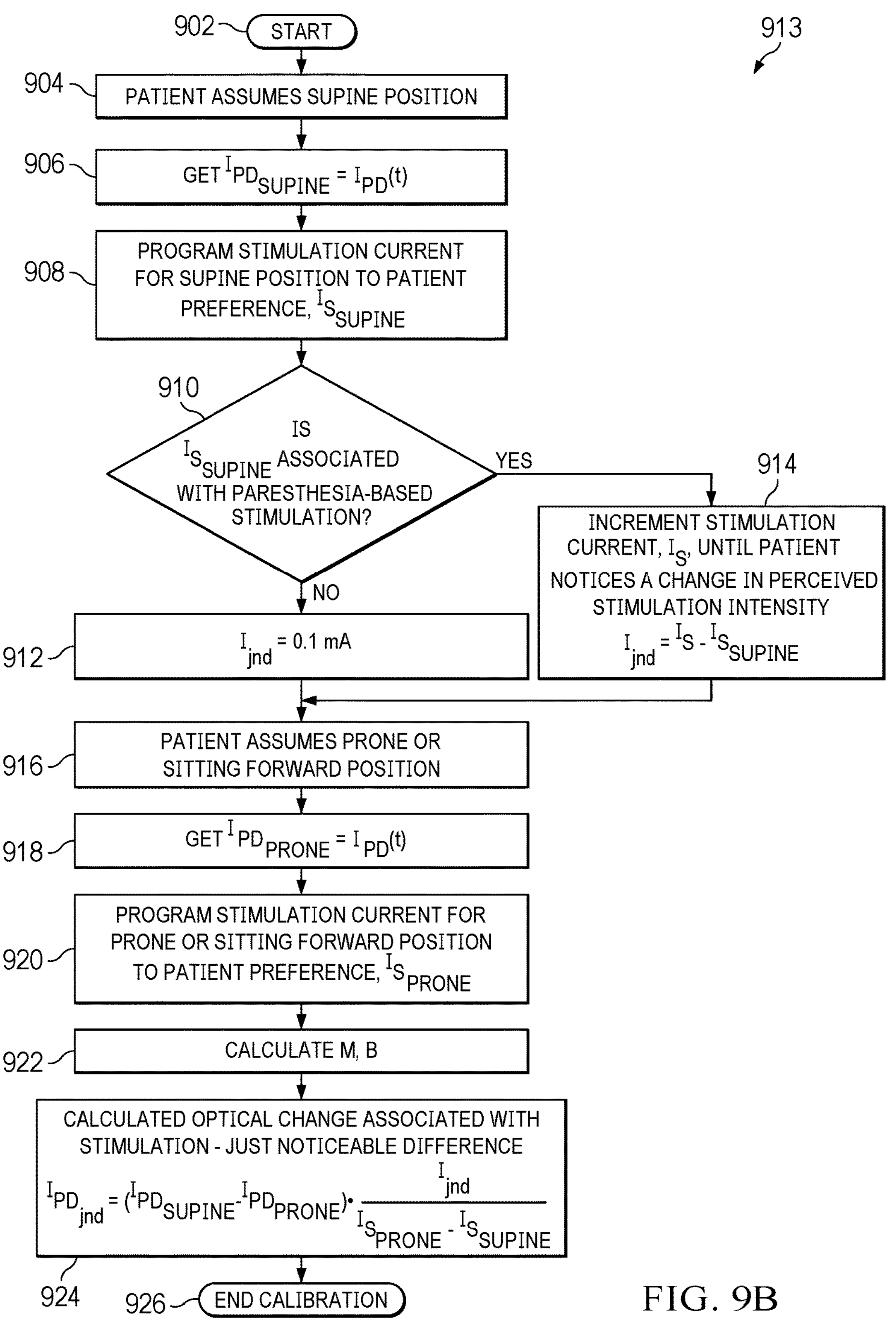
FIG. 9B is a flowchart of a preferred embodiment of a calibration state.

Referring then to FIG. 9B, a preferred embodiment of calibrate state 913, will be further described.

At step 902, IPG 510 is found in a wait state in which it polls RF transceiver 610 for instructions from external system manager 516.

At step 904, the patient assumes the supine position. Preferably, the patient's position is indicated to the external system manager by a selection received from input device 640. This selection is communicated from the external system manager to the IPG wirelessly.

At step 906, IPG 510 reads the photo diode current, $I_{PD}(t)$, and stores it in memory as "$I_{PDsupine}$"

At step 908, the stimulation current $I_{Ssupine}$ is manually adjusted to patient preference for the supine position through an input to external system manager 516, which is then communicated to IPG 510. IPG 510 then stores the value for $I_{Ssupine}$.

At step 910, external system manager 516 receives an indication as to whether or not paresthesia-based stimulation should be used. If so, the method moves to step 914. If not, the method moves to step 912.

At step 914, the stimulation current, $I_S$, is manually incremented until the patient notices a change in perceived stimulation intensity. This change can be thought of as a "just noticeable difference" or "JND". When such a change is indicated, the external system manager receives an input which is then forwarded to the IPG. The IPG records the stimulation current as $I_{JND}$ which is defined as $I_S - I_{Ssupine}$. The method then moves to step 916.

At step 912, $I_{JND}$ is set equal to the resolution of the pulse modulator resolution, preferably 0.1 mA.

At step 916, the patient assumes a prone or sitting forward position. Preferably, external system manager 516 receives a signal from input device 640 indicating that the patient has assumed such a position. External system manager 516 then sends a signal to IPG 510 indicating that the patient has assumed the prone or sitting forward position.

At step 918, IPG 510 reads the photo diode current, $I_{PD}(t)$, and stores it in memory as "$I_{PDprone}$".

At step 920, the stimulation current for the prone or sitting forward position is then programmed to patient preference. Preferably, external system manager 516 receives input which gradually increments the stimulation current. This input is sent to IPG 510 wirelessly which increments the stimulation current accordingly. When patient preference is reached, the external system manager receives a signal and forwards it to the IPG, where the stimulation current level $I_{Sprone}$ is stored.

At step 922, the linear coefficients M, and B, as previously defined, are calculated, by the IPG, and stored in memory.

At step 924, the optical change associated with the just noticeable difference stimulation is calculated according to the following equation, by the IPG.

$$I_{PDjnd} = (I_{PDsupine} - I_{PDprone}) \times \left( \frac{I_{JND}}{I_{Sprone} - I_{Ssupine}} \right)$$

At step 926, the method concludes, and the IPG and the external system manager both return to a wait state.

Figure 9C:
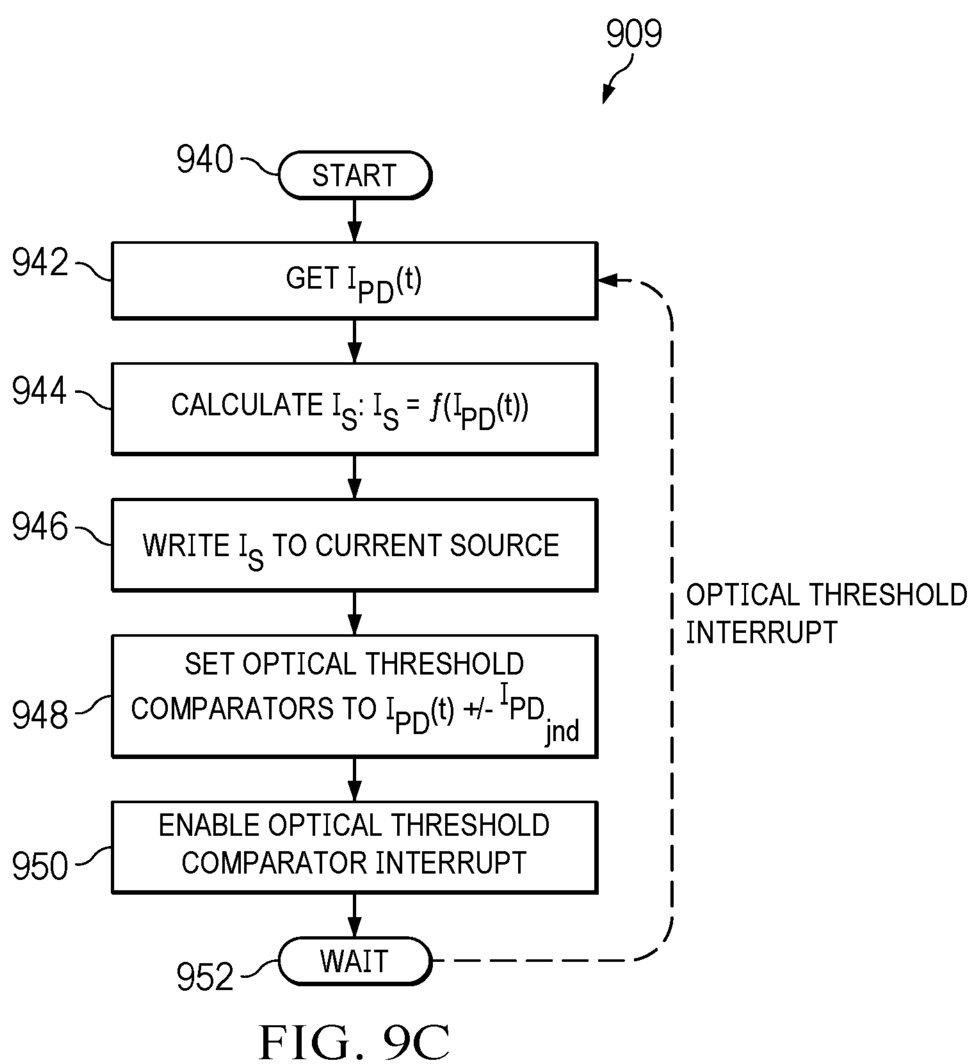
FIG. 9C is a flowchart of a preferred embodiment of a run state.

Referring them to FIG. 9C, "run" state 909 will be further described.

At step 940, the method begins.

At step 942, controller 505 retrieves the photo diode current $I_{PD}(t)$.

At step 944, the controller calculates the stimulation current $I_S$ as a function of the photo diode current $I_{PD}(t)$. A suitable transfer function is described by the following set of equations.

For $I_{PDprone} \leq I_{PD}(t) \leq I_{PDsupine}$:

$$I_S = M \times I_{PD}(t) + B$$

For $I_{PD}(t) \leq I_{PDprone}$ $$I_S = I_{Sprone}$$

For $I_{PD}(t) \geq I_{PDsupine}$ $$I_S = I_{Ssupine}$$

Where:

M and B assume the form as previously described.

At step 946, the controller writes the stimulation current value, $I_S$, to the current source, thereby activating the stimulation current to the electrodes.

At step 948, the controller sets the optical threshold comparator boundaries of control circuit 603 according to the following equations.

$$\text{Upper Optical Threshold} = I_{PD}(t) + I_{PDjnd}$$

$$\text{Lower Optical Threshold} = I_{PD}(t) - I_{PDjnd}$$

At step 950, the controller enables the optical threshold comparator interrupt of control circuit 603, as previously described.

At step 952, the controller waits for the control circuit to send an optical comparator interrupt. Upon receiving such an interrupt, the controller returns to step 942 and repeats the process.

Figure 9D:
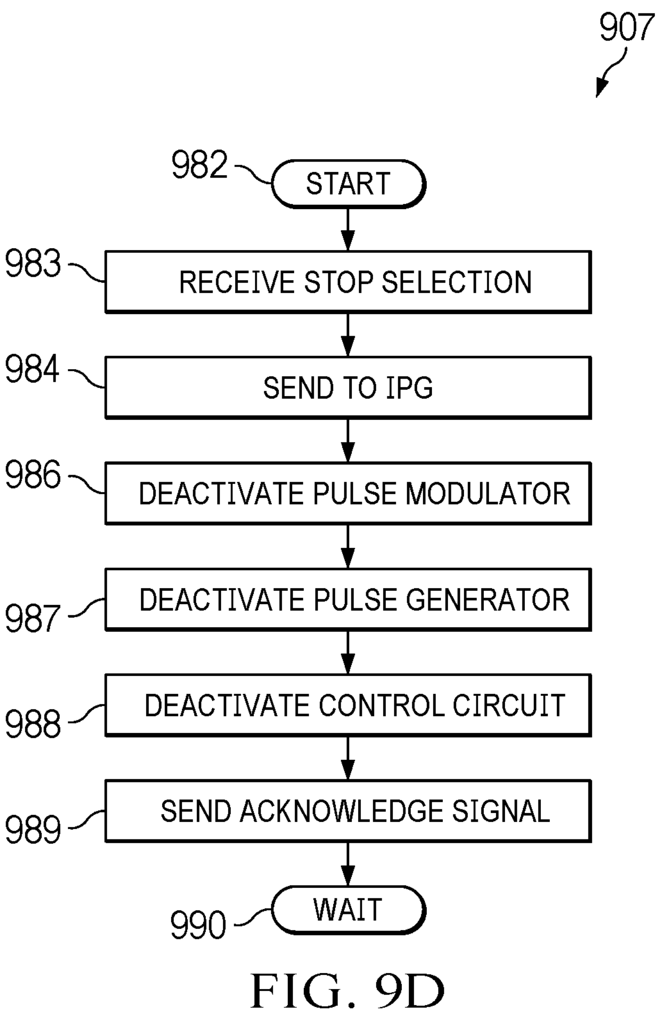
FIG. 9D is a flowchart of a preferred embodiment of a stop state.

Referring to FIG. 9D, "stop" state 907 will be further described.

At step 982, the method begins.

At step 983, external system manager 516 receives a "stop" selection from input device 640.

At step 984, external system manager 516 sends a stop command to IPG 510.

At step 986, CPU 602 deactivates pulse modulator 608.

At step 987, CPU 602 deactivates pulse generator 606.

At step 988, CPU 602 deactivates control circuit 603.

At step 989, IPG 510 sends an acknowledge signal to external system manager 516, indicating system stop.

At step 990, the method concludes and both the external system manager and the IPG return to a wait state.

The invention claimed is:

1. A system for stimulating a spinal cord of a patient comprising:

a controller, having a memory;

a reflectometer, operatively connected to the controller;

a stimulation electrode operatively connected to the controller; and a set of instructions, resident in the memory that, when executed cause the system to perform the steps of:

storing a lower reflectometer current boundary and an upper stimulation current boundary corresponding to a patient prone position, wherein the patient prone position is any posture of the patient in which the stimulation electrode is implanted wherein the spinal cord is in its most ventral position and further away from the reflectometer;

storing an upper reflectometer current boundary and a lower stimulation current boundary corresponding to a patient supine position, wherein the patient supine position is any posture of the patient in which the stimulation electrode is implanted wherein the spinal cord is in its most dorsal position and nearest the reflectometer;

deriving a functional relationship between the lower reflectometer current boundary, the upper reflectometer current boundary, the lower stimulation current boundary and the upper stimulation current boundary;

deriving an adjusted stimulation current value by adjusting a stimulation current value based on the functional relationship and a reflectometer current signal;

sending a stimulation signal to the stimulation electrode based on the adjusted stimulation current value; and directly applying the stimulation signal with the adjusted stimulation current value to a tissue of the patient.

2. The system of claim 1, wherein the functional relationship is linear.

3. The system of claim 1, wherein the set of instructions further comprises instructions that when executed cause the system to perform the step of:

clipping the reflectometer current signal at the upper reflectometer current boundary and the lower reflectometer current boundary, thereby maintaining the stimulation signal between the lower stimulation current boundary and the upper stimulation current boundary.

4. The system of claim 1, wherein the set of instructions further comprises instructions that when executed cause the system to perform the step of:

monitoring a processor interrupt condition for one of the upper reflectometer current boundary and the lower reflectometer current boundary.

5. The system of claim 4, wherein the set of instructions further comprises instructions that when executed cause the system to perform the step of:

changing the stimulation current value upon an occurrence of the processor interrupt condition.

6. The system of claim 1, wherein the set of instructions further comprises instructions that when executed cause the system to perform the step of:

setting an optical threshold comparator of the controller to respond to a range in the reflectometer current signal.

7. The system of claim 6, wherein the range is associated with a minimal difference in the stimulation signal.

8. A method for stimulating a spinal cord of a patient, the method further comprising:

providing a controller, having a memory;

providing a reflectometer, operatively connected to the controller;

providing a stimulation electrode operatively connected to the controller; and providing a set of instructions, resident in the memory that, when executed cause the controller to perform the steps of:

storing a lower reflectometer current boundary and an upper stimulation current boundary corresponding to a patient prone position, wherein the patient prone position is any posture of the patient in which the stimulation electrode is implanted wherein the spinal cord is in its most ventral position and further away from the reflectometer;

storing an upper reflectometer current boundary and a lower stimulation current boundary corresponding to a patient supine position, wherein the patient supine position is any posture of the patient in which the stimulation electrode is implanted wherein the spinal cord is in its most dorsal position and nearest the reflectometer;

deriving a functional relationship between the lower reflectometer current boundary, the upper reflectometer current boundary, the lower stimulation current boundary and the upper stimulation current boundary;

deriving an adjusted stimulation current value by adjusting a stimulation current value based on the functional relationship and a reflectometer current signal;

sending a stimulation signal to the stimulation electrode based on the adjusted stimulation current value; and directly applying the stimulation signal with the adjusted stimulation current value to a tissue of the patient.

9. The method of claim 8, wherein the functional relationship is linear.

10. The method of claim 8, wherein the set of instructions further comprises instructions that when executed further cause the controller to perform the steps of:

clipping the reflectometer current signal at one of the upper reflectometer current boundary and the lower reflectometer current boundary.

11. The method of claim 8, wherein the set of instructions further comprises instructions that when executed further cause the controller to perform the step of:

monitoring a processor interrupt condition for one of the upper reflectometer current boundary and the lower reflectometer current boundary.

12. The method of claim 11, wherein the set of instructions further comprises instructions that when executed further cause the controller to perform the step of:

changing the stimulation current value upon an occurrence of the processor interrupt condition.

13. The method of claim 8, wherein the set of instructions further comprises instructions that when executed further cause the controller to perform the step of:

setting an optical threshold comparator of the controller to respond to a range in the reflectometer current signal.

14. The method of claim 13, wherein the range is associated with a minimal difference in the stimulation signal.

* * * * *